United States Patent [19]

Hellring et al.

[11] Patent Number: 5,639,931

[45] Date of Patent: Jun. 17, 1997

[54] PROCESS FOR PRODUCING LOW AROMATIC DIESEL FUEL WITH HIGH CETANE INDEX

[75] Inventors: Stuart D. Hellring, Yardley; Albin Huss, Jr., Chadds Ford, both of Pa.; Michael E. Landis, Sewell; David O. Marler, Deptford, both of N.J.; Gerald J. Teitman, Vienna, Va.; Hye Kyung C. Timken, Woodbury, N.J.; Jeffrey C. Trewella, Kennett Square, Pa.

[73] Assignee: Mobil Oil Corporation, Fairfax, Va.

[21] Appl. No.: 459,062

[22] Filed: Jun. 2, 1995

Related U.S. Application Data

[63] Continuation-in-part of Ser. No. 442,549, May 16, 1995, which is a continuation-in-part of Ser. No. 205,437, Mar. 4, 1994, Pat. No. 5,437,855, which is a continuation-in-part of Ser. No. 137,705, Oct. 18, 1993, abandoned.

[51] Int. Cl.$^6$ .................................................. C07C 2/58
[52] U.S. Cl. ................................................................ 585/722
[58] Field of Search ...................................................... 585/722

[56] References Cited

U.S. PATENT DOCUMENTS

| | | | |
|---|---|---|---|
| 4,922,048 | 5/1990 | Harandi | 585/310 |
| 4,922,051 | 5/1990 | Nemet-Mavrodin et al. | 585/418 |
| 5,258,569 | 11/1993 | Chu et al. | 585/722 |
| 5,365,000 | 11/1994 | Kresge et al. | 585/722 |
| 5,437,855 | 8/1995 | Valyocsik | 423/718 |
| 5,461,182 | 10/1995 | Hellring et al. | 585/722 |

FOREIGN PATENT DOCUMENTS

WO 94/03415  2/1994  WIPO .................................. 585/722

OTHER PUBLICATIONS

Hydrocarbon Processing, vol. 60, No. 9, Sep. 1981, pp. 134–138.

Hydrocarbon Processing, vol. 61, No. 5, May 1982, pp. 110–112.

*Primary Examiner*—Glenn A. Caldarola
*Assistant Examiner*—Walter D. Griffin
*Attorney, Agent, or Firm*—Malcolm D. Keen; Thomas W. Steinberg

[57] ABSTRACT

At least one olefin and at least one isoparaffin are converted to a diesel fuel blending component by contacting the olefin and the isoparaffin with a catalyst selected from MCM-22, MCM-36, MCM-49, and MCM-56 to provide a product containing a diesel fuel.

15 Claims, No Drawings

PROCESS FOR PRODUCING LOW AROMATIC DIESEL FUEL WITH HIGH CETANE INDEX

CROSS REFERENCE TO RELATED APPLICATIONS

This application is a continuation in part of U.S. application Ser. No. 08/442,549, filed May 16, 1995 which is a continuation in part of U.S. application Ser. No. 08/205,437, filed Mar. 4, 1994, now U.S. Pat. No. 5,437,855, which is a continuation in part of U.S. application Ser. No. 08/137,705, filed Oct. 18, 1993, now abandoned, all of which are incorporated by reference as if set forth at length herein.

FIELD OF THE INVENTION

The present invention relates to a process for producing low aromatic diesel fuel with a high cetane index. Particularly, the invention relates to a process for selectively upgrading lower boiling range feedstocks into higher boiling range fuels having a desired composition.

BACKGROUND OF THE INVENTION

Recent regulatory developments have led refiners to seek methods for reformulating motor fuels, including gasoline and diesel fuel, to meet increasingly stringent air quality requirements. These techniques include reducing the olefin and aromatic content of the motor fuels while maintaining the desired operational characteristics as predicted by the octane or cetane rating of the fuel.

Alkylation is a reaction in which an alkyl group is added to an organic molecule. Thus an isoparaffin can be reacted with an olefin to provide an isoparaffin of higher molecular weight. Industrially, the concept depends on the reaction of a $C_2$ to $C_5$ olefin with isobutane in the presence of an acidic catalyst producing a so-called alkylate.

Industrial alkylation processes have historically used large volumes of liquid Bronsted acid catalysts such as hydrofluoric or sulfuric acid under relatively low temperature conditions. Acid strength is preferably maintained at 88 to 94 weight percent by the continuous addition of fresh acid and the continuous withdrawal of spent acid. Liquid acid catalyzed isoparaffin:olefin alkylation processes share inherent drawbacks including environmental and safety concerns, acid consumption, and sludge disposal. For a general discussion of sulfuric acid alkylation, see the series of three articles by L. F. Albright et al., "Alkylation of Isobutane with $C_4$ Olefins", 27 *Ind. Eng. Chem. Res.*, 381–397, (1988). For a survey of hydrofluoric acid catalyzed alkylation, see 1 *Handbook of Petroleum Refining Processes* 23–28 (R. A. Meyers, ed., 1986).

The typical petroleum refinery generates numerous olefinic streams, which, upon hydrogenation and optional fractionation, would be useful gasoline blending components. Examples of such streams include the olefinic gasoline and naphtha byproducts of catalytic hydrodewaxing processes such as the MLDW (Mobil Lubricant Dewaxing) and MDDW (Mobil Distillate Dewaxing). Additional examples include olefinic gasoline cuts from delayed coking units (thermally cracked gasoline), as well as from catalytic cracking process units such as a Fluidized Catalytic Cracking (FCC) process. Lighter olefins may be easily dimerized or oligomerized to provide suitable feedstocks, for example in a process such as MOGD/MOGDL (Mobil Olefins to Gasoline and Distillate/Mobil Olefins to Gasoline, Distillate and Lube Stock), or MOCI (Mobil Olefins to Chemical Intermediates). Examples of processes which produce olefinic stocks include the processes taught in U.S. Pat. Nos. 4,922,048 to Harandi and 4,922,051 to Nemet-Mavrodin et al. Additional examples of light olefin dimerization/oligomerization processes include Dimersol (light olefin dimerization), Isopol (selective isobutene isomerization) and Selectopol (selective butadiene polymerization). See *Hydrocarbon Processing*, Vol. 61, No. 5, May 1982, pp. 110–112, and *Hydrocarbon Processing*, Vol. 60, No. 9, September 1981, pp. 134–138.

Recent regulatory changes have created an incentive for refiners to reduce the olefins and aromatics content of motor fuels. The final version of the complex model issued by the United States Environmental Protection Agency (US EPA) to predict the consequence of various fuel components on combustion emissions creates a significant penalty for high RVP components in gasoline. At the same time, both the US EPA and state regulatory boards such as the California Air Resources Board (CARB) have instituted regulations on diesel fuel which set an upper limit on aromatics and sulfur contents, and a lower limit for cetane index. In general, sulfur must remain below 500 ppm. U.S. EPA requires either less than 35 wt % aromatics or a minimum of 40 cetane index. CARB limits aromatics to 10 wt % unless a waiver fuel is approved. Both regulatory agencies require a maximum $T_{90}$ of 640° F. By alkylating light olefins, such as $C_3$-$C_5$ olefins, with light isoparaffins, such as isobutane and isopentane, high RVP gasoline components are converted into more desirable products including lower RVP gasolines and diesel fuels which meet many of the regulatory restrictions now under consideration.

SUMMARY OF THE INVENTION

A mixed stream of isoparaffin, such as isobutane or isopentane, and olefins, such as propylene, butenes, pentenes, or hexenes, are passed over a zeolite catalyst such as MCM-22, MCM-36, MCM-49, or MCM-56 in a fixed-bed under pressure at sufficiently high temperature to produce diesel range fuel.

The feed olefins can come from among many sources including FCC olefins, MTBE raffinate, TAME raffinate, etc. A detailed description of possible olefins sources is outlined in U.S. Pat. No. 5,227,552, to Chang, Hellring and Striebel, which is incorporated by reference as if set forth at length herein. The isoparaffin can come from FCC, hydrocracking, etc. process or by isolation of field production off-gases.

The reaction temperature can be limited to obtain a range of aromatics content in the diesel fuel. To produce a diesel range blending stock containing less than about 10 wt % aromatics, the reactor temperature is preferably kept below about 375° F. To meet the 35 wt % aromatics limit set by the US EPA, reactor temperature is preferably controlled below about 440° F. In a preferred embodiment, the process conditions are controlled to produce a distillate product containing less than about 35 weight percent aromatics, and more preferably less than about 10 weight percent aromatics.

In general, higher cetane index of the diesel range product is favored by higher olefin WHSV and lower temperatures. However, products produced over a broad range of conversion conditions useful in the present process exceeded a cetane index of 35, and typically met the US EPA minimum of 40 cetane index. Under preferred conversion conditions, the distillate product cetane index was 45 or higher.

Conversion is inversely proportional with $\text{WHSV}_{olefin\ on\ zeolite}$ for a given temperature. Between 0.1 and 1.0 WHSV, reactor temperature must be above about 350° F. in order to achieve $C_5$-olefin conversions above 90%. If temperature is restricted to 375° F. to limit aromatics to 10 wt %, WHSV on zeolite must be held below about 0.3 to maintain 90% or greater pentenes conversion.

The term "yield" as used herein is defined as the weight of product per weight of converted olefin. Total product yields above unity indicate that isoparaffin has been incorporated into the products. Maximum gasoline yield in isobutane/butene alkylation results from combination of one mole of each reactant to provide a yield slightly above 2.0. Ideally, a diesel range fuel is produced by reacting more than one mole of olefin per isoparaffin. For instance, a mole of isobutane must combine with two or three moles of butene to reach sufficient molecular weight to enter the boiling range of diesel fuel. Likewise, a mole of isopentane would require two moles of pentene to reach diesel range and would give a yield of about 1.5. Therefore, diesel production in the present invention utilizes a lower isoparaffin/olefin molar ratio than typically is used for producing gasoline from a similar reactor feed stream.

Reaction products boiling at a cut point up to about 450° F. may be recycled to the contacting step. Preferably, reaction products boiling at a cut point up to about 390° F. may be recycled to the contacting step.

DETAILED DESCRIPTION

Feedstocks

Olefinic feedstocks suitable for use in the present invention include numerous olefinic streams produced by petroleum refining operations, for example, a cracked olefinic stream such as an olefinic gasoline boiling range fraction from a delayed coker process unit. Delayed coking processes are taught in U.S. Pat. No. 3,917,564 to Meyers and U.S. Pat. No. 4,874,505 to Bartilucci et al., both of which patents are incorporated herein by reference.

Suitable olefinic feedstocks are also produced as byproducts in catalytic dewaxing processes, as described in U.S. Pat. No. 4,922,048, which patent is incorporated herein by reference.

Catalytic dewaxing of hydrocarbon oils to reduce the temperature at which precipitation of waxy hydrocarbons occurs is a known process and is described, for example, in the Oil and Gas Journal, Jan. 6, 1975, pages 69–73. A number of patents have also described catalytic dewaxing processes. For example, U.S. Pat. No. 28,398 describes a process for catalytic dewaxing with a catalyst comprising a medium-pore zeolite and a hydrogenation/dehydrogenation component. U.S. Pat. No. 3,956,102 describes a process for hydrodewaxing a gas oil with a medium-pore zeolite catalyst. U.S. Pat. No. 4,100,056 describes a Mordenite catalyst containing a Group VI or a Group VIII metal which may be used to dewax a distillate derived from a waxy crude. U.S. Pat. No. 3,755,138 describes a process for mild solvent dewaxing to remove high quality wax from a lube stock, which is then catalytically dewaxed to specification pour point. Such developments in catalytic dewaxing have led to the MLDW (Mobil Lube Dewaxing) and MDDW (Mobil Distillate Dewaxing) process.

Catalytic dewaxing processes may be followed by other processing steps such as hydrodesulfurization and denitrogenation in order to improve the qualities of the product. For example, U.S. Pat. No. 3,668,113 describes a catalytic dewaxing process employing a Mordenite dewaxing catalyst which is followed by a catalytic hydrodesulfurization step over an alumina-based catalyst. U.S. Pat. No. 4,400,265 describes a catalytic dewaxing/hydrodewaxing process using a zeolite catalyst having the structure of ZSM-5 wherein gas oil is catalytically dewaxed followed by hydrodesulfurization in a cascade system. The foregoing dewaxing processes exemplify low-severity medium-pore catalyzed dewaxing processes which produce a low octane naphtha by-product. Another example of a low severity medium-pore catalyzed conversion reaction is olefin oligomerization.

Recent developments in zeolite catalysts and hydrocarbon conversion methods and apparatuses have created interest in utilizing olefinic feedstocks for producing heavier hydrocarbons, such as $C_5+$ gasoline, distillate or lubes. These developments form the basis of the Mobil olefins to gasoline/distillate (MOGD) method and apparatus, and the Mobil olefins to gasoline/distillate/lubes (MOGDL) method and apparatus.

In MOGD and MOGDL, olefins are catalytically converted to heavier hydrocarbons by catalytic oligomerization using an acid crystalline zeolite, such as a zeolite catalyst having the structure of ZSM-5. Process conditions can be varied to favor the formation of either gasoline, distillate or lube range products. U.S. Pat. Nos. 3,960,978 and 4,021,502 to Plank et al. disclose the conversion of $C_2$-$C_5$ olefins alone or in combination with paraffinic components, into higher hydrocarbons over a crystalline zeolite catalyst. U.S. Pat. Nos. 4,150,062; 4,211,640 and 4,227,992 to Garwood et al. have contributed improved processing techniques to the MOGD system. U.S. Pat. No. 4,456,781 to Marsh et al. has also disclosed improved processing techniques for the MOGD system.

U.S. Pat. Nos. 4,422,185 and 4,483,760 to Tabak disclose two-stage catalytic processes for upgrading hydrocarbon feedstocks, the texts of which are incorporated by reference as if set forth at length herein.

The '185 patent to Tabak teaches a process for converting an olefinic feedstock containing ethene and heavier alkenes to a product rich in distillate and olefinic gasoline. Effluent from a first stage distillate mode reactor is flashed to separate an ethylene-rich product stream which is then charged to a second stage gasoline mode reactor. A disadvantage of the process taught by '185 is that the highly olefinic gasoline product stream is of a relatively low octane and reduces the gasoline pool octane.

The '760 patent to Tabak teaches a process for catalytically dewaxing a middle distillate separating an olefinic by-product from the dewaxed distillate product stream, and upgrading a gasoline fraction at temperatures above 900° F. In addition, the second catalytic reactor is operated to convert at least 10 wt. % of the olefinic by-product fraction to fuel oil (material boiling above 380° F.).

Olefinic feedstocks may be obtained from various sources, including from fossil fuel processing streams such as gas separation units, from the cracking of $C_2$-hydrocarbons, such as LPG (liquified petroleum gas) from coal by-products, from various synthetic fuel processing streams, and as by-products from fluid catalytic cracking (FCC) and thermal catalytic cracking (TCC) process units. U.S. Pat. No. 4,100,218 to Chen et al. teaches thermal cracking of ethane to ethylene, with subsequent conversion of ethylene to LPG and gasoline over a zeolite catalyst having the structure of ZSM-5.

The catalysts useful in the present invention may comprise one or more members of the group consisting of MCM-22, MCM-36, MCM-49, and MCM-56.

MCM-22 is taught in U.S. Pat. Nos. 4,992,615; 5,012,033; 5,073,665 and 5,107,047.

MCM-36 is taught in U.S. Pat. Nos. 4,250,277; 5,258,569 and 5,292,698.

MCM-49 is taught in U.S. Pat. Nos. 5,236,575; 5,254,792 and 5,354,718.

MCM-56 is taught in U.S. Pat. No. 5,362,697.

The large pore crystalline molecular sieves which can be used in the present invention include those which absorb 2,2,4-trimethylpentane. Representative large pore crystalline molecular sieves include, for example, the following zeolites: ZSM-3, ZSM-4, ZSM-12, ZSM-18, ZSM-20, zeolite L, mordenite, faujasite, zeolite Y, and the rare earth metal-containing forms of the above-listed zeolites. Zeolite Beta can also be used in the present invention, although it is understood that zeolite Beta may exhibit characteristics of a medium-pore zeolite or a large-pore zeolite depending upon process conditions.

Zeolites having an effective pore size of generally from about 5 to about 8 Angstroms, such as to freely sorb normal hexane, are also useful support materials in the process of the invention. A convenient measure of the extent to which a zeolite provides control to molecules of varying sizes to its internal structure is the Constraint Index of the zeolite. The method by which the Constraint Index is determined is described in U.S. Pat. No. 4,016,218, incorporated herein by reference for details of the method. U.S. Pat. No. 4,696,732 discloses Constraint Index values for typical zeolite materials and is incorporated by reference as if set forth at length herein.

Both inert and catalytically active supports may be employed, with examples including one or more of alumina, silica, silica-alumina, zeolites, clays, Kieselguhr, titania, magnesia and active carbons from sources such as coal, coke, and coconut shell. Supports such as active carbon, alumina, silica, and silica-alumina are preferred, with active carbon being most preferred. Active carbon is useful in the present invention in the presence or absence of added catalytic metal, and may be activated and/or regenerated by selective oxidation with air or peroxides, fluorine, or sulfur oxides. Activation may also be effected by treatment with caustic, fluorine compounds such as HF and CsF, phosphoric acid, sulfuric acid, zinc chloride, potassium sulfide, and/or steam. Hydrogen, carbon oxides, or mixtures thereof, may also be used for activation.

The metallic components useful as catalyst components in the process of the present invention include the metals (as well as the metallic oxides and sulfides) of Group VIII of the Periodic Table of the Elements, which Table is shown at the back inside cover of F. A. Cotton and G. Wilkinson Advanced *Inorganic Chemistry A Comprehensive Text*, John Wiley and Sons, 1980. Platinum, iridium, nickel, and palladium (as well as the oxides and sulfides thereof) are preferred, and palladium is particularly preferred.

| Process Conditions | | |
|---|---|---|
| | Broad Range | Preferred Range |
| Temperature | 100–500° F. | 200–400° F. |
| Pressure | 0–1500 psig | 50–1000 psig |
| LHSV | 0.01–10 | 0.1–5.0 |
| Olefin:Paraffin Molar Ratio in Feedstock | 0.1–100 | 0.25–50 |

EXAMPLES

Example 1. The catalyst used in this example was an extrudate of the proton-form of MCM-56 (65%) in an alumina binder (35%). The catalyst (2.92 g,7.1 ml) was loaded into a stainless steel tubular reactor and bracketed by vycor chips which served as heat exchangers. After placing the reactor in a tube furnace, the catalyst was dried by heating for at least two hours to at least 300° F. in a stream of flowing nitrogen. The reactor temperature was adjusted to 370° F. at 600 psig, and filled with isobutane. A pre-mixed isobutane/butene-2 feed stream (molar ratio=1) then was introduced at a flow rate of 0.57 gm butene/gmMCM-56/hr. After passing pre-mixed feed through the reactor zone for 49 hrs, product was collected over the following 28 hrs. Product distributions were calculated from gc analyses of the gaseous and liquid products, and an additional simulated distillation ASTM 2887 of the liquid products. The total reactor effluent weight was 58.7 g (97.7% mass balance) and showed the following distribution:

| Component | weight % |
|---|---|
| $C_3$-minus | 0.00 |
| Isobutane | 43.18 |
| n-Butane | 0.00 |
| Isopentane | 3.57 |
| n-Pentane | 0.00 |
| Cyclopentane | 0.96 |
| $C_6$-paraffin | 0.44 |
| Methylcyclopentane | 1.44 |
| $C_4$-olefin | 0.00 |
| Butadiene | 0.14 |
| $C_5$-olefin | 0.00 |
| Cyclopentene | 0.00 |
| $C_6$-olefin | 3.03 |
| Methylcyclopentane and Benzene | 0.02 |
| $C_7$-plus | 47.21 |
| Total | 100.00 |

Conversion of total butenes was 97.1%. Calculated yields of C5-plus components per butenes converted (wt/wt) were:

| Fraction | Yields |
|---|---|
| $C_5$ | 0.08 |
| $C_6$–300° F. | 0.51 |
| 300–400° F. | 0.21 |
| 400–650° F. | 0.30 |
| above 650° F. | 0.04 |
| Total | 1.14 |

About 25 g of squalane was added to a portion of the liquid product (34.6 g) to serve as a high boiling "chaser" during fractional microdistillation. After distilling the sample to a 300° F. endpoint at ambient atmospheric pressure, the residua were fractionated under vacuum (about 55 torr) to obtain a cut (4.3 g) with the intended kerojet boiling range from 300° F. to 400° F. The actual boiling range for this cut was estimated by simulated distillation analysis ASTM 2887. The boiling range and product properties for this sample were:

| Intended cut 300–400° F. | |
|---|---|
| Boiling Range (°F.) | |
| BP | 218 |
| T10 | 237 |
| T50 | 353 |
| T90 | 403 |
| EP | 459 |
| API gravity | 54.3 |
| Cetane Index | 53 |
| Cetane Number ($^1$H nmr) | 19 |

After cooling, the residua were again distilled under vacuum (about 1–2 torr) to obtain a cut (9.4 g) with the intended diesel fuel boiling range from 400° F. to 650° F. The actual boiling range for this cut was estimated by simulated distillation analysis ASTM 2887. The boiling range and product properties for this sample were:

| Intended cut 400–650° F. | |
|---|---|
| Boiling Range (°F.) | |
| IBP | 330 |
| T10 | 386 |
| T50 | 473 |
| T90 | 581 |
| EP | 655 |
| API gravity | 42.6 |
| Cetane Index | 55 |
| Cetane Number ($^1$H nmr) | 19 |
| wt % Aromatics | 8.4 |

Example 2. This example was performed with the catalyst from the previous example by adjusting the reactor temperature to 302° F. at 600 psig. A pre-mixed isobutane/butene-2 feed stream (molar ratio=1) then was introduced at a flow rate of 1.02 gm butene/gmMCM-56/hr. After passing pre-mixed feed through the reactor zone for 44.5 hrs, product was collected over the following 24 hrs. Product distributions were calculated from gc analyses of the gaseous and liquid products, and an additional simulated distillation ASTM 2887 of the liquid products. The total reactor effluent weight was 92.4 g (99.3% mass balance) and showed the following distribution:

| Component | weight % |
|---|---|
| $C_3$-minus | 0.00 |
| Isobutane | 46.96 |
| n-Butane | 0.98 |
| Isopentane | 0.34 |
| n-Pentane | 0.09 |
| Cyclopentane | 0.00 |
| $C_6$-paraffin | 0.06 |
| Methylcyclopentane | 0.02 |
| $C_4$-olefin | 16.64 |
| Butadiene | 0.01 |
| $C_5$-olefin | 0.03 |
| Cyclopentene | 0.00 |
| $C_6$-olefin | 0.24 |
| Methylcyclopentane and Benzene | 0.01 |
| $C_7$-plus | 34.65 |
| Total | 100.00 |

Conversion of total butenes was 66.7%. Calculated yields of C5-plus components per butenes converted (wt/wt) were:

| Fraction | Yields |
|---|---|
| $C_5$ | 0.01 |
| $C_6$–300° F. | 0.74 |
| 300–400° F. | 0.22 |
| 400–650° F. | 0.09 |
| above 650° F. | 0.00 |
| Total | 1.06 |

About 25 g of squalane was added to a portion of the liquid product (36.1 g) to serve as a high boiling "chaser" during fractional microdistillation. After distilling the sample to a 300° F. endpoint at ambient atmospheric pressure, the residua were fractionated under vacuum (about 55 torr) to obtain a cut (8.1 g) with the intended kerojet boiling range from 300° F. to 400° F. The actual boiling range for this cut was estimated by simulated distillation analysis ASTM 2887. The boiling range and product properties for this sample were:

| Intended cut 300–400° F. | |
|---|---|
| Boiling Range (°F.) | |
| BP | 219 |
| T10 | 243 |
| T50 | 320 |
| T90 | 391 |
| EP | 433 |
| API gravity | 54.2 |
| Cetane Index | 42 |
| Cetane Number ($H^1$ nmr) | 11 |

After cooling, the residua were again distilled under vacuum (about 1–2 torr) to obtain a cut (3.4 g) with the intended diesel fuel boiling range from 400° F. to 650° F. The actual boiling range for this cut was estimated by simulated distillation analysis ASTM 2887. The boiling range and product properties for this sample were:

| Intended cut 400–650° F. | |
|---|---|
| Boiling Range (°F.) | |
| IBP | 344 |
| T10 | 381 |
| T50 | 456 |
| T90 | 507 |
| EP | 575 |
| API gravity | 44.9 |
| Cetane Index | 57 |
| Cetane Number ($^1$H nmr) | 15 |
| wt % Aromatics | 1.5 |

Example 3. The catalyst used in this example was an extrudate of the proton-form of MCM-56 (65%) in an alumina binder (35%). The catalyst (2.92 g, 7.1 ml) was loaded into a stainless steel tubular reactor and bracketed by vycor chips which served as heat exchangers. After placing the reactor in a tube furnace, the catalyst was dried by heating for at least two hours to at least 300° F. in a stream of flowing nitrogen. The reactor temperature was adjusted to 450° F. at 600 psig, and filled with isobutane. A pre-mixed isobutane/butene-2 feed stream (molar ratio=1) then was introduced at a flow rate of 1 gm butene/gm MCM-56/hr. After passing pre-mixed feed through the reactor zone for 41.5 hrs, product was collected over the following 23.3 hrs. Product distributions were calculated from gc analyses of the gaseous and liquid products, and an additional simulated distillation ASTM 2887 of the liquid products. The total reactor effluent weight was 88.1 g (99.4% mass balance) and showed the following distribution:

| Component | weight % |
|---|---|
| $C_3$-minus | 0.17 |
| Isobutane | 42.48 |
| n-Butane | 1.24 |
| Isopentane | 7.30 |
| n-Pentane | 0.00 |
| Cyclopentane | 0.01 |
| $C_6$-paraffin | 2.42 |
| Methylcyclopentane | 0.55 |
| $C_4$-olefin | 0.91 |
| Butadiene | 0.00 |
| $C_5$-olefin | 0.33 |
| Cyclopentene | 0.00 |

-continued

| Component | weight % |
|---|---|
| $C_6$-olefin | 4.21 |
| Methylcyclopentane and Benzene | 0.02 |
| $C_7$-plus | 40.35 |
| Total | 100.00 |

Conversion of total butenes was 98.2%. Calculated yields of $C_5$-plus components per butenes converted (wt/wt) were:

| Fraction | Yields |
|---|---|
| $C_5$ | 0.16 |
| $C_6$–300° F. | 0.58 |
| 300–400° F. | 0.15 |
| 400–650° F. | 0.24 |
| above 650° F. | 0.01 |
| Total | 1.13 |

About 25 g of squalane was added to a portion of the liquid product (53.6 g) to serve as a high boiling "chaser" during fractional microdistillation. After distilling the sample to a 300° F. endpoint at ambient atmospheric pressure, the residua were fractionated under vacuum (about 55 torr) to obtain a cut (6.4 g) with the intended kerojet boiling range from 300° F. to 400° F. The actual boiling range for this cut was estimated by simulated distillation analysis ASTM 2887. The boiling range properties for this sample were:

| Intended cut 300–400° F. | |
|---|---|
| Boiling Range (°F.) | |
| BP | 194 |
| T10 | 242 |
| T50 | 343 |
| T90 | 406 |
| EP | 451 |
| API gravity | 55.8 |
| Cetane Index | 53 |
| Cetane Number ($^1$H nmr) | 19 |

After cooling, the residua were again distilled under vacuum (about 1–2 torr) to obtain a cut (10.3 g) with the intended diesel fuel boiling range from 400° F. to 650° F. The actual boiling range for this cut was estimated by simulated distillation analysis ASTM 2887. The boiling range and product properties for this sample were:

| Intended cut 400–650° F. | |
|---|---|
| Boiling Range (°F.) | |
| IBP | 334 |
| T10 | 398 |
| T50 | 493 |
| T90 | 610 |
| EP | 684 |
| API gravity | 39.5 |
| Cetane Index | 52 |
| Cetane Number ($^1$H nmr) | 25 |
| wt % Aromatics | 26.6 |

Example 4. This example was performed with the catalyst from the previous example by adjusting the reactor temperature to 300° F. at 600 psig. A pre-mixed isobutane/butene-2 feed stream (molar ratio=1) then was introduced at a flow rate of 0.11 gm butene/gm MCM-56/hr. After passing pre-mixed feed through the reactor zone for 313.3 hrs, product was collected over the following 191.5 hrs. Product distributions were calculated from gc analyses of the gaseous and liquid products, and an additional simulated distillation ASTM 2887 of the liquid products. The total reactor effluent weight was 75.6 g (96.2% mass balance) and showed the following distribution:

| Component | weight % |
|---|---|
| $C_3$-minus | 0.02 |
| Isobutane | 43.72 |
| n-Butane | 0.81 |
| Isopentane | 0.57 |
| n-Pentane | 0.00 |
| Cyclopentane | 0.33 |
| $C_6$-paraffin | 0.28 |
| Methylcyclopentane | 0.00 |
| $C_4$-olefin | 1.47 |
| Butadiene | 0.01 |
| $C_5$-olefin | 0.13 |
| Cyclopentene | 0.00 |
| $C_6$-olefin | 0.57 |
| Methylcyclopentane and Benzene | 0.06 |
| $C_7$-plus | 52.04 |
| Total | 100.00 |

Conversion of total butenes was 98.2%. Calculated yields of $C_5$-plus components per butenes converted (wt/wt) were:

| Fraction | Yields |
|---|---|
| $C_5$ | 0.02 |
| $C_6$–300° F. | 0.58 |
| 300–400° F. | 0.30 |
| 400–650° F. | 0.22 |
| above 650° F. | 0.00 |
| Total | 1.12 |

About 25 g of squalane was added to a portion of the liquid product (43.8 g) to serve as a high boiling "chaser" during fractional microdistillation. After distilling the sample to a 300° F. endpoint at ambient atmospheric pressure, the residua were fractionated under vacuum (about 55 torr) to obtain a cut (8.0 g) with the intended kerojet boiling range from 300° F. to 400° F. The actual boiling range for this cut was estimated by simulated distillation analysis ASTM 2887. The boiling range and product properties for this sample were:

| Intended cut 300–400° F. | |
|---|---|
| Boiling Range (°F.) | |
| BP | 228 |
| T10 | 263 |
| T50 | 380 |
| T90 | 414 |
| EP | 491 |
| API gravity | 52.3 |
| Cetane Index | 56 |
| Cetane Number ($^1$H nmr) | 13 |

After cooling, the residua were again distilled under vacuum (about 1–2 torr) to obtain a cut (8.3 g) with the intended diesel fuel boiling range from 400° F. to 650° F. The actual boiling range for this cut was estimated by simulated distillation analysis ASTM 2887. The boiling range and product properties for this sample were:

| Intended cut 400–650° F. | |
|---|---|
| Boiling Range (°F.) | |
| IBP | 356 |
| T10 | 398 |
| T50 | 475 |
| T90 | 550 |
| EP | 628 |
| API gravity | 44.2 |
| Cetane Index | 58 |
| Cetane Number ($^1$H nmr) | 18 |
| wt % Aromatics | 2.1 |

Example 5. The catalyst used in this example was an extrudate of the proton-form of MCM-56 (65%) in an alumina binder (35%). The catalyst (3.23 g, 7.1 ml) was loaded into a stainless steel tubular reactor and bracketed by vycor chips which served as heat exchangers. After placing the reactor in a tube furnace, the catalyst was dried by heating for at least two hours to at least 300° F. in a stream of flowing nitrogen. The reactor temperature was adjusted to 450° F. at 600 psig, and filled with isobutane. A pre-mixed isobutane/butene-2 feed stream (molar ratio=1) then was introduced at a flow rate of 1 gm butene/gm MCM-56/hr. After passing pre-mixed feed through the reactor zone for 319.5 hrs, product was collected over the following 159 hrs. Product distributions were calculated from gc analyses of the gaseous and liquid products, and an additional simulated distillation ASTM 2887 of the liquid products. The total reactor effluent weight was 62.8 g (96.2% mass balance) and showed the following distribution:

| Component | weight % |
|---|---|
| $C_3$-minus | 0.10 |
| Isobutane | 27.08 |
| n-Butane | 1.63 |
| Isopentane | 10.19 |
| n-Pentane | 0.04 |
| Cyclopentane | 0.00 |
| $C_6$-paraffin | 5.65 |
| Methylcyclopentane | 0.80 |
| $C_4$-olefin | 0.21 |
| Butadiene | 0.00 |
| $C_5$-olefin | 0.07 |
| Cyclopentene | 0.00 |
| $C_6$-olefin | 0.53 |
| Methylcyclopentane and Benzene | 0.03 |
| $C_7$-plus | 53.67 |
| Total | 100.00 |

Conversion of total butenes was 99.6%. Calculated yields of $C_5$-plus components per butenes converted (wt/wt) were:

| Fraction | Yields |
|---|---|
| $C_5$ | 0.21 |
| $C_6$–300° F. | 0.68 |
| 300–400° F. | 0.19 |
| 400–650° F. | 0.27 |
| above 650° F. | 0.08 |
| Total | 1.43 |

About 25 g of squalane was added to a portion of the liquid product (43.0 g) to serve as a high boiling "chaser" during fractional microdistillation. After distilling the sample to a 300° F. endpoint at ambient atmospheric pressure, the residua were fractionated under vacuum (about 55 torr) to obtain a cut (4.6 g) with the intended kerojet boiling range from 300° F. to 400° F. The actual boiling range for this cut was estimated by simulated distillation analysis ASTM 2887. The boiling range and product properties for this sample were:

| Intended cut 300–400° F. | |
|---|---|
| Boiling Range (°F.) | |
| BP | 137 |
| T10 | 228 |
| T50 | 282 |
| T90 | 385 |
| EP | 436 |
| API gravity | 60.6 |
| Cetane Index | 43 |
| Cetane Number ($^1$H nmr) | 28 |

After cooling, the residua were again distilled under vacuum (about 1–2 torr) to obtain a cut (6.6 g) with the intended diesel fuel boiling range from 400° F. to 650° F. The actual boiling range for this cut was estimated by simulated distillation analysis ASTM 2887. The boiling range and product properties for this sample were:

| Intended cut 400–650° F. | |
|---|---|
| Boiling Range (°F.) | |
| IBP | 310 |
| T10 | 386 |
| T50 | 479 |
| T90 | 591 |
| EP | 655 |
| API gravity | 35.8 |
| Cetane Index | 44 |
| Cetane Number ($^1$H nmr) | 27 |
| wt % Aromatics | 44.3 |

Example 6. This example was performed with the catalyst from the previous example by adjusting the reactor temperature to 369° F. at 600 psig. A pre-mixed isobutane/butene-2 feed stream (molar ratio=1) then was introduced at a flow rate of 0.5 gm butene/gm MCM-56/hr. After passing pre-mixed feed through the reactor zone for 74 hrs, product was collected over the following 28.5 hrs. Product distributions were calculated from gc analyses of the gaseous and liquid products, and an additional simulated distillation ASTM 2887 of the liquid products. The total reactor effluent weight was 61.0 g (101.4% mass balance) and showed the following distribution:

| Component | weight % |
|---|---|
| $C_3$-minus | 0.12 |
| Isobutane | 29.21 |
| n-Butane | 1.48 |
| Isopentane | 7.89 |
| n-Pentane | 0.03 |
| Cyclopentane | 0.00 |
| $C_6$-paraffin | 4.36 |
| Methylcyclopentane | 0.61 |
| $C_4$-olefin | 0.18 |
| Butadiene | 0.00 |
| $C_5$-olefin | 0.06 |
| Cyclopentene | 0.00 |
| $C_6$-olefin | 0.41 |
| Methylcyclopentane and Benzene | 0.02 |
| $C_7$-plus | 55.63 |
| Total | 100.00 |

Conversion of total butenes was 99.6%. Calculated yields of $C_5$-plus components per butenes converted (wt/wt) were:

| Fraction | Yields |
|---|---|
| C5 | 0.16 |
| C$_6$-300° F. | 0.66 |
| 300–400° F. | 0.28 |
| 400–650° F. | 0.27 |
| above 650° F. | 0.01 |
| Total | 1.39 |

About 25 g of squalane was added to a portion of the liquid product (35.8 g) to serve as a high boiling "chaser" during fractional microdistillation. After distilling the sample to a 300° F. endpoint at ambient atmospheric pressure, the residua were fractionated under vacuum (about 55 torr) to obtain a cut (6.8 g) with the intended kerojet boiling range from 300° F. to 400° F. The actual boiling range for this cut was estimated by simulated distillation analysis ASTM 2887. The boiling range and product properties for this sample were:

| Intended cut 300–400° F. | |
|---|---|
| Boiling Range (°F.) | |
| BP | 219 |
| T10 | 271 |
| T50 | 372 |
| T90 | 407 |
| EP | 441 |
| API gravity | 52.9 |
| Cetane Index | 55 |
| Cetane Number ($_1$ nmr) | 14 |

After cooling, the residua were again distilled under vacuum (about 1–2 torr) to obtain a cut (6.8 g) with the intended diesel fuel boiling range from 400° F. to 650° F. The actual boiling range for this cut was estimated by simulated distillation analysis ASTM 2887. The boiling range and product properties for this sample were:

| Intended cut 400–650° F. | |
|---|---|
| Boiling Range (°F.) | |
| IBP | 344 |
| T10 | 394 |
| T50 | 468 |
| T90 | 555 |
| EP | 634 |
| API gravity | 43.8 |
| Cetane Index | 57 |
| Cetane Number ($^1$H nmr) | 13 |
| wt % Aromatics | 4.2 |

Example 7. The catalyst used in this example was an extrudate of the proton-form of MCM-56 (65%) in an alumina binder (35%). The catalyst (11.35 g,28 ml) was loaded into a stainless steel tubular reactor and bracketed by vycor chips which served as heat exchangers. After placing the reactor in a tube furnace, the catalyst was dried by heating for at least two hours to at least 300° F. in a stream of flowing nitrogen. The reactor temperature was adjusted to 377° F. at 600 psig, and filled with isopentane. A pre-mixed isopentane/pentene-1 feed stream (molar ratio=4.9) then was introduced at a flow rate of 0.56 gm pentenes/gmMCM-56/hr. After passing pre-mixed feed through the reactor zone for 5.8 hrs, product was collected over the following 14.0 hrs. Product distributions were calculated from gc analyses of the gaseous and liquid products, and a simulated distillation ASTM 2887 of the residua after rotory evaporation (85° C., ambient atmospheric pressure) of the total liquid products. The total reactor effluent weight was 343.5 g (99.5% mass balance) and showed the following distribution:

| Component | weight % |
|---|---|
| C$_3$-minus | 0.03 |
| Isobutane | 2.98 |
| n-Butane | 0.04 |
| Isopentane | 74.07 |
| n-Pentane | 0.94 |
| Cyclopentane | 0.00 |
| C$_6$-paraffin | 2.88 |
| Methylcyclopentane | 0.02 |
| C$_4$-olefin | 0.03 |
| Butadiene | 0.01 |
| C$_5$-olefin | 0.59 |
| Cyclopentene | 0.00 |
| C$_6$-olefin | 0.40 |
| Methylcyclopentane and Benzene | 0.00 |
| C$_7$-plus | 18.00 |
| Total | 100.00 |

Conversion of total C$_5$-olefins was 96.4%. Calculated yields of isobutane and C$_6$-plus components per C$_5$-olefins converted (wt/wt) were:

| Fraction | Yields |
|---|---|
| iC4 | 0.19 |
| C$_6$-300° F. | 0.42 |
| 300–400° F. | 0.45 |
| 400–650° F. | 0.37 |
| above 650° F. | 0.08 |
| Total | 1.51 |

About 25 g of squalane was added to a portion (61.2 g) of the rotory evaporation residua to serve as a high boiling "chaser" during fractional microdistillation. After distilling the sample to a 300° F. endpoint at ambient atmospheric pressure, the resulting residua were cooled, then fractionated under vacuum (about 55 torr) to obtain a cut (21.0 g) with the intended kerojet boiling range from 300° F. to 400° F. The actual boiling range for this cut was estimated by simulated distillation analysis ASTM 2887. The boiling range and product properties for this sample were:

| Intended cut 300–400° F. | |
|---|---|
| Boiling Range (°F.) | |
| BP | 222 |
| T10 | 286 |
| T50 | 325 |
| T90 | 363 |
| EP | 427 |
| API gravity | 57.7 |
| Cetane Index | 52 |
| Cetane Number ($^1$H nmr) | 25 |

After cooling, the resulting residua were again distilled under vacuum (about 1–2 torr) to obtain a cut (14.3 g) with the intended diesel fuel boiling range from 400° F. to 650° F. The actual boiling range for this cut was estimated by simulated distillation analysis ASTM 2887. The boiling range and product properties for this sample were:

| Intended cut 400–650° F. | |
| --- | --- |
| Boiling Range (°F.) | |
| IBP | 340 |
| T10 | 410 |
| T50 | 482 |
| T90 | 571 |
| EP | 625 |
| API gravity | 42.8 |
| Cetane Index | 57 |
| Cetane Number ($^1$H nmr) | 29 |
| wt % Aromatics | 7.1 |

Example 8. This example was performed with the catalyst from the previous example by adjusting the reactor temperature to 304° F. at 600 psig. A pre-mixed isopentane/pentene-1 feed stream (molar ratio=9.8) then was introduced at a flow rate of 1.01 gm pentenes/gm MCM-56/hr. After passing pre-mixed feed through the reactor zone for 6.2 hrs, product was collected over the following 4.0 hrs. Product distributions were calculated from gc analyses of the gaseous and liquid products, and a simulated distillation ASTM 2887 of the residua after rotory evaporation (85° C., ambient atmospheric pressure) of the total liquid products. The total reactor effluent weight was 330.7 g (100.6% mass balance) and showed the following distribution:

| Component | weight % |
| --- | --- |
| $C_3$-minus | 0.00 |
| Isobutane | 0.17 |
| n-Butane | 0.01 |
| Isopentane | 88.97 |
| n-Pentane | 0.36 |
| Cyclopentane | 0.00 |
| $C_6$-paraffin | 0.13 |
| Methylcyclopentane | 0.01 |
| $C_4$-olefin | 0.01 |
| Butadiene | 0.02 |
| $C_5$-olefin | 7.11 |
| Cyclopentene | 0.00 |
| $C_6$-olefin | 0.02 |
| Methylcyclopentane and Benzene | 0.00 |
| $C_7$-plus | 3.20 |
| Total | 100.00 |

Conversion of total $C_5$-olefins was 21.5%. Calculated yields of isobutane and $C_6$-plus components per $C_5$-olefins converted (wt/wt) were:

| Fraction | Yields |
| --- | --- |
| iC4 | 0.09 |
| $C_6$-300° F. | 0.18 |
| 300–400° F. | 1.09 |
| 400–650° F. | 0.47 |
| above 650° F. | 0.00 |
| Total | 1.83 |

About 25 g of squalane was added to a portion (7.2 g) of the rotory evaporation residua to serve as a high boiling "chaser" during fractional microdistillation. After distilling the sample to a 300° F. endpoint at ambient atmospheric pressure, the resulting residua were cooled, then fractionated under vacuum (about 55 torr) to obtain a cut (3.8 g) with the intended kerojet boiling range from 300° F. to 400° F. The actual boiling range for this cut was estimated by simulated distillation analysis ASTM 2887. The boiling range and product properties for this sample were:

| Intended cut 300–400° F. | |
| --- | --- |
| Boiling Range (°F.) | |
| BP | 193 |
| T10 | 306 |
| T50 | 328 |
| T90 | 341 |
| EP | 446 |
| API gravity | 55.0 |
| Cetane Index | 46 |
| Cetane Number ($^1$H nmr) | 14 |

After cooling, the resulting residua were again distilled under vacuum (about 1–2 torr) to obtain a cut (0.9 g) with the intended diesel fuel boiling range from 400° F. to 650° F. The actual boiling range for this cut was estimated by simulated distillation analysis ASTM 2887. The boiling range and product properties for this sample were:

| Intended cut 400–650° F. | |
| --- | --- |
| Boiling Range (°F.) | |
| IBP | 302 |
| T10 | 326 |
| T50 | 467 |
| T90 | 519 |
| EP | 785 |
| API gravity | 44.6 |
| Cetane Index | 58 |
| Cetane Number ($^1$H nmr) | 23 |
| wt % Aromatics | <5 |

Example 9. This example was performed with the catalyst from the previous example by adjusting the reactor temperature to 449° F. at 600 psig. A pre-mixed isopentane/pentene-1 feed stream (molar ratio=9.9) then was introduced at a flow rate of 0.99 gm pentenes/gmMCM-56/hr. After passing pre-mixed feed through the reactor zone for 19.8 hrs, product was collected over the following 3.5 hrs. Product distributions were calculated from gc analyses of the gaseous and liquid products, and a simulated distillation ASTM 2887 of the residua after rotory evaporation (85° C., ambient atmospheric pressure) of the total liquid products. The total reactor effluent weight was 282.7 g (99.0% mass balance) and showed the following distribution:

| Component | weight % |
| --- | --- |
| $C_3$-minus | 0.03 |
| Isobutane | 2.03 |
| n-Butane | 0.04 |
| Isopentane | 87.25 |
| n-Pentane | 0.35 |
| Cyclopentane | 0.03 |
| $C_6$-paraffin | 2.35 |
| Methylcyclopentane | 0.16 |
| $C_4$-olefin | 0.10 |
| Butadiene | 0.02 |
| $C_5$-olefin | 1.18 |
| Cyclopentene | 0.00 |
| $C_6$-olefin | 0.60 |
| Methylcyclopentane and Benzene | 0.05 |
| $C_7$-plus | 5.81 |
| Total | 100.00 |

Conversion of total $C_5$-olefins was 86.9%. Calculated yields of isobutane and $C_6$-plus components per $C_5$-olefins converted (wt/wt) were:

| Fraction | Yields |
|---|---|
| iC4 | 0.26 |
| $C_6$–300° F. | 0.57 |
| 300–400° F. | 0.29 |
| 400–650° F. | 0.25 |
| above 650° F. | 0.03 |
| Total | 1.40 |

About 25 g of squalane was added to a portion (16.9 g) of the rotory evaporation residua to serve as a high boiling "chaser" during fractional microdistillation. After distilling the sample to a 300° F. endpoint at ambient atmospheric pressure, the resulting residua were cooled, then fractionated under vacuum (about 55 torr) to obtain a cut (4.8 g) with the intended kerojet boiling range from 300° F. to 400° F. The actual boiling range for this cut was estimated by simulated distillation analysis ASTM 2887. The boiling range and product properties for this sample were:

| Intended cut 300–400° F. | |
|---|---|
| Boiling Range (°F.) | |
| BP | 173 |
| T10 | 267 |
| T50 | 324 |
| T90 | 375 |
| EP | 444 |
| API gravity | 55.0 |
| Cetane Index | 45 |
| Cetane Number ($^1$H nmr) | 17 |

After cooling, the resulting residua were again distilled under vacuum (about 1–2 torr) to obtain a cut (3.1 g) with the intended diesel fuel boiling range from 400° F. to 650 ° F. The actual boiling range for this cut was estimated by simulated distillation analysis ASTM 2887. The boiling range and product properties for this sample were:

| Intended cut 400–650° F. | |
|---|---|
| Boiling Range (°F.) | |
| IBP | 315 |
| T10 | 371 |
| T50 | 471 |
| T90 | 564 |
| EP | 634 |
| API gravity | 38.2 |
| Cetane Index | 47 |
| Cetane Number ($^1$H nmr) | 25 |
| wt % Aromatics | 46.7 |

Example 10. This example was performed with the catalyst from the previous example by adjusting the reactor temperature to 444° F. at 600 psig. A pre-mixed isopentane/pentene-1 feed stream (molar ratio=1.0) then was introduced at a flow rate of 0.10 gm pentenes/gm MCM-56/hr. After passing pre-mixed feed through the reactor zone for 87.3 hrs, product was collected over the following 48.2 hrs. Product distributions were calculated from gc analyses of the gaseous and liquid products, and a simulated distillation ASTM 2887 of the residua after rotory evaporation (85° C., ambient atmospheric pressure) of the total liquid products.

The total reactor effluent weight was 72.1 g (100.1% mass balance) and showed the following distribution:

| Component | weight % |
|---|---|
| $C_3$-minus | 0.19 |
| Isobutane | 10.18 |
| n-Butane | 0.25 |
| Isopentane | 38.87 |
| n-Pentane | 1.29 |
| Cyclopentane | 0.14 |
| $C_6$-paraffin | 12.99 |
| Methylcyclopentane | 0.24 |
| $C_4$-olefin | 0.05 |
| Butadiene | 0.01 |
| $C_5$-olefin | 0.41 |
| Cyclopentene | 0.00 |
| $C_6$-olefin | 1.10 |
| Methylcyclopentane and Benzene | 0.08 |
| $C_7$-plus | 34.21 |
| Total | 100.00 |

Conversion of total $C_5$-olefins was 99.2%. Calculated yields of isobutane and $C_6$-plus components per $C_5$-olefins converted (wt/wt) were:

| Fraction | Yields |
|---|---|
| iC4 | 0.21 |
| $C_6$–300° F. | 0.42 |
| 300–400° F. | 0.46 |
| 400–650° F. | 0.09 |
| above 650° F. | 0.01 |
| Total | 1.19 |

About 25 g of squalane was added to a portion (28.1 g) of the rotory evaporation residua to serve as a high boiling "chaser" during fractional microdistillation. After distilling the sample to a 300° F. endpoint at ambient atmospheric pressure, the resulting residua were cooled, then fractionated under vacuum (about 55 torr) to obtain a cut (5.6 g) with the intended kerojet boiling range from 300° F. to 400° F. The actual boiling range for this cut was estimated by simulated distillation analysis ASTM 2887. The boiling range and product properties for this sample were:

| Intended cut 300–400° F. | |
|---|---|
| Boiling Range (°F.) | |
| BP | 133 |
| T10 | 235 |
| T50 | 322 |
| T90 | 381 |
| EP | 439 |
| API gravity | 56.9 |
| Cetane Index | 49 |
| Cetane Number ($^1$H nmr) | 31 |

After cooling, the resulting residua were again distilled under vacuum (about 1–2 torr) to obtain a cut (6.6 g) with the intended diesel fuel boiling range from 400° F. to 650 ° F. The actual boiling range for this cut was estimated by simulated distillation analysis ASTM 2887. The boiling range and product properties for this sample were:

| Intended cut 400–650° F. | |
|---|---|
| Boiling Range (°F.) | |
| IBP | 311 |
| T10 | 385 |
| T50 | 488 |
| T90 | 592 |
| EP | 659 |
| API gravity | 33.3 |
| Cetane Index | 41 |
| Cetane Number ($^1$H nmr) | 28 |
| wt % Aromatics | 45.9 |

Example 11. This example was performed with the catalyst from the previous example by adjusting the reactor temperature to 374° F. at 600 psig. A pre-mixed isopentane/pentene-1 feed stream (molar ratio=4.9) then was introduced at a flow rate of 0.56 gm pentenes/gm MCM-56/hr. After passing pre-mixed feed through the reactor zone for 8.0 hrs, product was collected over the following 14.5 hrs. Product distributions were calculated from gc analyses of the gaseous and liquid products, and a simulated distillation ASTM 2887 of the residua after rotory evaporation (85° C., ambient atmospheric pressure) of the total liquid products. The total reactor effluent weight was 358.7 g (100.4% mass balance) and showed the following distribution:

| Component | weight % |
|---|---|
| $C_3$-minus | 0.02 |
| Isobutane | 0.70 |
| n-Butane | 0.08 |
| Isopentane | 81.84 |
| n-Pentane | 0.54 |
| Cyclopentane | 0.06 |
| $C_6$-paraffin | 2.43 |
| Methylcyclopentane | 0.36 |
| $C_4$-olefin | 0.12 |
| Butadiene | 0.02 |
| $C_5$-olefin | 5.72 |
| Cyclopentene | 0.00 |
| $C_6$-olefin | 1.04 |
| Methylcyclopentane and Benzene | 0.11 |
| $C_7$-plus | 6.97 |
| Total | 100.00 |

Conversion of total $C_5$-olefins was 65.6%. Calculated yields of isobutane and $C_6$-plus components per $C_5$-olefins converted (wt/wt) were:

| Fraction | Yields |
|---|---|
| iC4 | 0.06 |
| $C_6$–300° F. | 0.53 |
| 300–400° F. | 0.16 |
| 400–650° F. | 0.21 |
| above 650° F. | 0.11 |
| Total | 1.07 |

About 25 g of squalane was added to a portion (27.7 g) of the rotory evaporation residua to serve as a high boiling "chaser" during fractional microdistillation. After distilling the sample to a 300° F. endpoint at ambient atmospheric pressure, the resulting residua were cooled, then fractionated under vacuum (about 55 torr) to obtain a cut (8.5 g) with the intended kerojet boiling range from 300° F. to 400 ° F. The actual boiling range for this cut was estimated by simulated distillation analysis ASTM 2887. The boiling range and product properties for this sample were:

| Intended cut 400–650° F. | |
|---|---|
| Boiling Range (°F.) | |
| IBP | 311 |
| T10 | 385 |
| T50 | 488 |
| T90 | 592 |
| EP | 659 |
| API gravity | 33.3 |
| Cetane Index | 41 |
| Cetane Number ($^1$H nmr) | 28 |
| wt % Aromatics | 45.9 |

After cooling, the resulting residua were again distilled under vacuum (about 1–2 torr) to obtain a cut (2.7 g) with the intended diesel fuel boiling range from 400° F. to 650 ° F. The actual boiling range for this cut was estimated by simulated distillation analysis ASTM 2887. The boiling range and product properties for this sample were:

| Intended cut 400–650° F. | |
|---|---|
| Boiling Range (°F.) | |
| IBP | 314 |
| T10 | 367 |
| T50 | 466 |
| T90 | 539 |
| EP | 633 |
| API gravity | 39.2 |
| Cetane Index | 48 |
| Cetane Number ($^1$H nmr) | 18 |
| wt % Aromatics | 9.1 |

Example 12. The catalyst used in this example was an extrudate of the proton-form of MCM-56 (65%) in an alumina binder (35%). The catalyst (12.72 g,29 ml) was loaded into a stainless steel tubular reactor and bracketed by vycor chips which served as heat exchangers. After placing the reactor in a tube furnace, the catalyst was dried by heating for at least two hours to at least 300° F. in a stream of flowing nitrogen. The reactor temperature was adjusted to 297° F. at 600 psig, and filled with isopentane. A pre-mixed isopentane/pentene-1 feed stream (molar ratio=1.0) then was introduced at a flow rate of 0.10 gm pentenes/gmMCM-56/hr. After passing pre-mixed feed through the reactor zone for 77.5 hrs, product was collected over the following 49.0 hrs. Product distributions were calculated from gc analyses of the gaseous and liquid products, and a simulated distillation ASTM 2887 of the residua after rotory evaporation (85° C., ambient atmospheric pressure) of the total liquid products. The total reactor effluent weight was 80.5 g (98.7% mass balance) and showed the following distribution:

| Component | weight % |
|---|---|
| $C_3$-minus | 0.00 |
| Isobutane | 0.99 |
| n-Butane | 0.29 |
| Isopentane | 49.40 |
| n-Pentane | 1.62 |
| Cyclopentane | 0.28 |
| $C_6$-paraffin | 11.51 |
| Methylcyclopentane | 1.27 |
| $C_4$-olefin | 0.01 |
| Butadiene | 0.01 |

-continued

| Component | weight % |
|---|---|
| $C_5$-olefin | 0.62 |
| Cyclopentene | 0.00 |
| $C_6$-olefin | 0.80 |
| Methylcyclopentane and Benzene | 0.20 |
| $C_7$-plus | 33.00 |
| Total | 100.00 |

Conversion of total $C_5$-olefins was 98.7%. Calculated yields of isobutane and $C_6$-plus components per $C_5$-olefins converted (wt/wt) were:

| Fraction | Yields |
|---|---|
| iC4 | 0.02 |
| $C_6$–300° F. | 0.38 |
| 300–400° F. | 0.23 |
| 400–650° F. | 0.27 |
| above 650° F. | 0.07 |
| Total | 0.98 |

About 25 g of squalane was added to a portion (29.7 g) of the rotary evaporation residua to serve as a high boiling "chaser" during fractional microdistillation. After distilling the sample to a 300° F. endpoint at ambient atmospheric pressure, the resulting residua were cooled, then fractionated under vacuum (about 55 torr) to obtain a cut (7 g) with the intended kerojet boiling range from 300° F. to 400° F. The actual boiling range for this cut was estimated by simulated distillation analysis ASTM 2887. The boiling range and product properties for this sample were:

| Intended cut 300–400° F. | |
|---|---|
| Boiling Range (°F.) | |
| BP | |
| T10 | 132 |
| T50 | 246 |
| T90 | 326 |
| EP | 378 |
| | 453 |
| API gravity | 55.7 |
| Cetane Index | 48 |
| Cetane Number ($^1$H nmr) | 17 |

After cooling, the resulting residua were again distilled under vacuum (about 1–2 torr) to obtain a cut (8.8 g) with the intended diesel fuel boiling range from 400° F. to 650° F. The actual boiling range for this cut was estimated by simulated distillation analysis ASTM 2887. The boiling range and product properties for this sample were:

| Intended cut 400–650° F. | |
|---|---|
| Boiling Range (°F.) | |
| IBP | 308 |
| T10 | 370 |
| T50 | 487 |
| T90 | 589 |
| EP | 656 |
| API gravity | 41.0 |
| Cetane Index | 54 |

| Intended cut 400–650° F. | |
|---|---|
| Cetane Number ($^1$H nmr) | 21 |
| wt % Aromatics | 7.8 |

Example 13. This example was performed with the catalyst from the previous example by adjusting the reactor temperature to 296° F. at 600 psig. A pre-mixed isopentane/pentene-1 feed stream (molar ratio=9.8) then was introduced at a flow rate of 0.10 gm pentenes/gm MCM-56/hr. After passing pre-mixed feed through the reactor zone for 43.0 hrs, product was collected over the following 55.0 hrs. Product distributions were calculated from gc analyses of the gaseous and liquid products, and a simulated distillation ASTM 2887 of the residua after rotary evaporation (85° C., ambient atmospheric pressure) of the total liquid products. The total reactor effluent weight was 503.7 g (100.3% mass balance) and showed the following distribution:

| Component | weight % |
|---|---|
| $C_3$-minus | 0.03 |
| Isobutane | 0.17 |
| n-Butane | 0.01 |
| Isopentane | 88.55 |
| n-Pentane | 0.41 |
| Cyclopentane | 0.00 |
| $C_6$-paraffin | 0.10 |
| Methylcyclopentane | 0.02 |
| $C_4$-olefin | 0.04 |
| Butadiene | 0.00 |
| $C_5$-olefin | 6.01 |
| Cyclopentene | 0.00 |
| $C_6$-olefin | 0.23 |
| Methylcyclopentane and Benzene | 0.00 |
| $C_7$-plus | 4.42 |
| Total | 100.00 |

Conversion of total $C_5$-olefins was 33.2%. Calculated yields of isobutane and $C_6$-plus components per $C_5$-olefins converted (wt/wt) were:

| Fraction | Yields |
|---|---|
| iC4 | 0.06 |
| $C_6$–300° F. | 0.24 |
| 300–400° F. | 1.06 |
| 400–650° F. | 0.30 |
| above 650° F. | 0.00 |
| Total | 1.66 |

About 25 g of squalane was added to a portion (23.6 g) of the rotary evaporation residua to serve as a high boiling "chaser" during fractional microdistillation. After distilling the sample to a 300° F. endpoint at ambient atmospheric pressure, the resulting residua were cooled, then fractionated under vacuum (about 55 torr) to obtain a cut (11.6 g) with the intended kerojet boiling range from 300° F. to 400° F. The actual boiling range for this cut was estimated by simulated distillation analysis ASTM 2887. The boiling range and product properties for this sample were:

| Intended cut 300–400° F. | |
| --- | --- |
| Boiling Range (°F.) | |
| BP | 208 |
| T10 | 302 |
| T50 | 327 |
| T90 | 343 |
| EP | 454 |
| API gravity | 55.8 |
| Cetane Index | 48 |
| Cetane Number ($^1$H nmr) | 16 |

After cooling, the resulting residua were again distilled under vacuum (about 1–2 torr) to obtain a cut (4.3 g) with the intended diesel fuel boiling range from 400° F. to 650° F. The actual boiling range for this cut was estimated by simulated distillation analysis ASTM 2887. The boiling range and product properties for this sample were:

| Intended cut 400–650° F. | |
| --- | --- |
| Boiling Range (°F.) | |
| IBP | 300 |
| T10 | 324 |
| T50 | 461 |
| T90 | 507 |
| EP | 597 |
| API gravity | 46.3 |
| Cetane Index | 60 |
| Cetane Number ($^1$H nmr) | 20 |
| wt % Aromatics | <5 |

Example 14. This example was performed with the catalyst from the previous example by adjusting the reactor temperature to 377° F. at 600 psig. A pre-mixed isopentane/pentene-1 feed stream (molar ratio=5.0) then was introduced at a flow rate of 0.54 gm pentenes/gmMCM-56/hr. After passing pre-mixed feed through the reactor zone for 18.0 hrs, product was collected over the following 6.0 hrs. Product distributions were calculated from gc analyses of the gaseous and liquid products, and a simulated distillation ASTM 2887 of the residua after rotory evaporation (85° C., ambient atmospheric pressure) of the total liquid products. The total reactor effluent weight was 165.4 g (101.0% mass balance) and showed the following distribution:

| Component | weight % |
| --- | --- |
| $C_3$-minus | 0.34 |
| Isobutane | 2.18 |
| n-Butane | 0.81 |
| Isopentane | 74.98 |
| n-Pentane | 0.63 |
| Cyclopentane | 0.00 |
| $C_6$-paraffin | 2.03 |
| Methylcyclopentane | 0.00 |
| $C_4$-olefin | 0.02 |
| Butadiene | 0.01 |
| $C_5$-olefin | 0.90 |
| Cyclopentene | 0.00 |
| $C_6$-olefin | 0.39 |
| Methylcyclopentane and Benzene | 0.00 |
| $C_7$-plus | 17.70 |
| Total | 100.00 |

Conversion of total $C_5$-olefins was 94.5%. Calculated yields of isobutane and $C_6$-plus components per $C_6$-olefins converted (wt/wt) were:

| Fraction | Yields |
| --- | --- |
| iC4 | 0.14 |
| $C_6$–300° F. | 0.38 |
| 300–400° F. | 0.50 |
| 400–650° F. | 0.37 |
| above 650° F. | 0.04 |
| Total | 1.44 |

About 25 g of squalane was added to a portion (31.8 g) of the rotory evaporation residua to serve as a high boiling "chaser" during fractional microdistillation. After distilling the sample to a 300° F. endpoint at ambient atmospheric pressure, the resulting residua were cooled, then fractionated under vacuum (about 55 torr) to obtain a cut (11.0 g) with the intended kerojet boiling range from 300° F. to 400° F. The actual boiling range for this cut was estimated by simulated distillation analysis ASTM 2887. The boiling range and product properties for this sample were:

| Intended cut 300–400° F. | |
| --- | --- |
| Boiling Range (°F.) | |
| BP | 164 |
| T10 | 269 |
| T50 | 316 |
| T90 | 351 |
| EP | 428 |
| API gravity | 57.7 |
| Cetane Index | 49 |
| Cetane Number ($^1$H nmr) | 26 |

After cooling, the resulting residua were again distilled under vacuum (about 1–2 torr) to obtain a cut (8.3 g) with the intended diesel fuel boiling range from 400° F. to 650° F. The actual boiling range for this cut was estimated by simulated distillation analysis ASTM 2887. The boiling range and product properties for this sample were:

| Intended cut 400–650° F. | |
| --- | --- |
| Boiling Range (°F.) | |
| IBP | 302 |
| T10 | 372 |
| T50 | 471 |
| T90 | 575 |
| EP | 636 |
| API gravity | 43.3 |
| Cetane Index | 56 |
| Cetane Number ($^1$H nmr) | 27 |
| wt % Aromatics | 7.1 |

Example 15. This example was performed with the catalyst from the previous example by adjusting the reactor temperature to 302° F. at 600 psig. A pre-mixed isopentane/pentene-1 feed stream (molar ratio=1.0) then was introduced at a flow rate of 1.00 gm pentenes/gmMCM-56/hr. After passing pre-mixed feed through the reactor zone for 18.0 hrs, product was collected over the following 6.0 hrs. Product distributions were calculated from gc analyses of the gaseous and liquid products, and a simulated distillation ASTM 2887 of the residua after rotory evaporation (85° C., ambient atmospheric pressure) of the total liquid products. The total reactor effluent weight was 102.2 g (103.1% mass balance) and showed the following distribution:

| Component | weight % |
| --- | --- |
| C$_3$-minus | 0.09 |
| Isobutane | 0.99 |
| n-Butane | 0.00 |
| Isopentane | 50.81 |
| n-Pentane | 0.73 |
| Cyclopentane | 0.00 |
| C$_6$-paraffin | 0.00 |
| Methylcyclopentane | 0.00 |
| C$_4$-olefin | 0.00 |
| Butadiene | 0.00 |
| C$_5$-olefin | 38.20 |
| Cyclopentene | 0.00 |
| C$_6$-olefin | 0.00 |
| Methylcyclopentane and Benzene | 0.00 |
| C$_7$-plus | 9.19 |
| Total | 100.00 |

Conversion of total C$_5$-olefins was 23.9%. Calculated yields of isobutane and C$_6$-plus components per C$_5$-olefins converted (wt/wt) were:

| Fraction | Yields |
| --- | --- |
| iC4 | 0.08 |
| C$_6$–300° F. | 0.02 |
| 300–400° F. | 0.63 |
| 400–650° F. | 0.12 |
| above 650° F. | 0.00 |
| Total | 0.85 |

About 25 g of squalane was added to a portion (10.4 g) of the rotory evaporation residua to serve as a high boiling "chaser" during fractional microdistillation. After distilling the sample to a 300° F. endpoint at ambient atmospheric pressure, the resulting residua were cooled, then fractionated under vacuum (about 55 torr) to obtain a cut (5.7 g) with the intended kerojet boiling range from 300° F. to 400° F. The actual boiling range for this cut was estimated by simulated distillation analysis ASTM 2887. The boiling range and product properties for this sample were:

| Intended cut 300–400° F. | |
| --- | --- |
| Boiling Range (°F.) | |
| BP | 213 |
| T10 | 318 |
| T50 | 332 |
| T90 | 346 |
| EP | 418 |
| API gravity | 54.6 |
| Cetane Index | 47 |
| Cetane Number ($^1$H nmr) | 16 |

After cooling, the resulting residua were again distilled under vacuum (about 1–2 torr) to obtain a cut (1.3 g) with the intended diesel fuel boiling range from 400° F. to 650° F. The actual boiling range for this cut was estimated by simulated distillation analysis ASTM 2887. The boiling range and product properties for this sample were:

| Intended cut 400–650° F. | |
| --- | --- |
| Boiling Range (°F.) | |
| IBP | 309 |
| T10 | 325 |
| T50 | 474 |
| T90 | 498 |
| EP | 589 |
| API gravity | 45.3 |
| Cetane Index | 61 |
| Cetane Number ($^1$H nmr) | 22 |
| wt % Aromatics | 5.1 |

Example 16. This example was performed with the catalyst from the previous example by adjusting the reactor temperature to 458° F. at 600 psig. A pre-mixed isopentane/pentene-1 feed stream (molar ratio=1.0) then was introduced at a flow rate of 1.01 gm pentenes/gm MCM-56/hr. After passing pre-mixed feed through the reactor zone for 17.5 hrs, product was collected over the following 7.0 hrs. Product distributions were calculated from gc analyses of the gaseous and liquid products, and a simulated distillation ASTM 2887 of the residua after rotory evaporation (85° C., ambient atmospheric pressure) of the total liquid products. The total reactor effluent weight was 115.7 g (99.9% mass balance) and showed the following distribution:

| Component | weight % |
| --- | --- |
| C$_3$-minus | 0.09 |
| Isobutane | 6.31 |
| n-Butane | 0.05 |
| Isopentane | 39.79 |
| n-Pentane | 1.17 |
| Cyclopentane | 0.00 |
| C$_6$-paraffin | 6.93 |
| Methylcyclopentane | 0.42 |
| C$_4$-olefin | 0.06 |
| Butadiene | 0.00 |
| C$_5$-olefin | 0.72 |
| Cyclopentene | 0.00 |
| C$_6$-olefin | 0.62 |
| Methylcyclopentane and Benzene | 0.02 |
| C$_7$-plus | 43.81 |
| Total | 100.00 |

Conversion of total C$_5$-olefins was 98.6%. Calculated yields of isobutane and C$_6$-plus components per C$_5$-olefins converted (wt/wt) were:

| Fraction | Yields |
| --- | --- |
| iC4 | 0.13 |
| C6–300° F. | 0.36 |
| 300–400° F. | 0.27 |
| 400–650° F. | 0.30 |
| above 650° F. | 0.12 |
| Total | 1.17 |

About 25 g of squalane was added to a portion (56.8 g) of the rotory evaporation residua to serve as a high boiling "chaser" during fractional microdistillation. After distilling the sample to a 300° F. endpoint at ambient atmospheric pressure, the resulting residua were cooled, then fractionated under vacuum (about 55 torr) to obtain a cut (12.3 g) with the intended kerojet boiling range from 300° F. to 400° F.

The actual boiling range for this cut was estimated by simulated distillation analysis ASTM 2887. The boiling range and product properties for this sample were:

| Intended cut 300–400° F. | |
|---|---|
| Boiling Range (°F.) | |
| BP | 185 |
| T10 | 276 |
| T50 | 330 |
| T90 | 382 |
| EP | 445 |
| API gravity | 56.7 |
| Cetane Index | 51 |
| Cetane Number ($^1$H nmr) | 32 |

After cooling, the resulting residua were again distilled under vacuum (about 1–2 torr) to obtain a cut (15.2 g) with the intended diesel fuel boiling range from 400° F. to 650° F. The actual boiling range for this cut was estimated by simulated distillation analysis ASTM 2887. The boiling range and product properties for this sample were:

| Intended cut 400–650° F. | |
|---|---|
| Boiling Range (°F.) | |
| IBP | 315 |
| T10 | 395 |
| T50 | 495 |
| T90 | 596 |
| EP | 652 |
| API gravity | 38.3 |
| Cetane Index | 51 |
| Cetane Number ($^1$H nmr) | 31 |
| wt % Aromatics | 28.8 |

Example 17. This example was performed with the catalyst from the previous example by adjusting the reactor temperature to 450° F. at 600 psig. A pre-mixed isopentane/pentene-1 feed stream (molar ratio=9.8) then was introduced at a flow rate of 0.10 gm pentenes/gm MCM-56/hr. After passing pre-mixed feed through the reactor zone for 21.0 hrs, product was collected over the following 41.5 hrs. Product distributions were calculated from gc analyses of the gaseous and liquid products, and a simulated distillation ASTM 2887 of the residua after rotory evaporation (85° C., ambient atmospheric pressure) of the total liquid products. The total reactor effluent weight was 384.0 g (99.3% mass balance) and showed the following distribution:

| Component | weight % |
|---|---|
| $C_3$-minus | 0.01 |
| Isobutane | 4.91 |
| n-Butane | 0.00 |
| Isopentane | 82.16 |
| n-Pentane | 0.43 |
| Cyclopentane | 0.00 |
| $C_6$-paraffin | 1.96 |
| Methylcyclopentane | 0.00 |
| $C_4$-olefin | 0.01 |
| Butadiene | 0.00 |
| $C_5$-olefin | 0.27 |
| Cyclopentene | 0.00 |
| $C_6$-olefin | 1.78 |
| Methylcyclopentane and Benzene | 0.00 |

-continued

| Component | weight % |
|---|---|
| $C_7$-plus | 8.46 |
| Total | 100.00 |

Conversion of total $C_5$-olefins was 97.0%. Calculated yields of isobutane and $C_6$-plus components per $C_5$-olefins converted (wt/wt) were:

| Fraction | Yields |
|---|---|
| iC4 | 0.56 |
| $C_6$–300° F. | 0.70 |
| 300–400° F. | 0.36 |
| 400–650° F. | 0.28 |
| above 650° F. | 0.05 |
| Total | 1.96 |

About 25 g of squalane was added to a portion (36.3 g) of the rotory evaporation residua to serve as a high boiling "chaser" during fractional microdistillation. After distilling the sample to a 300° F. endpoint at ambient atmospheric pressure, the resulting residua were cooled, then fractionated under vacuum (about 55 torr) to obtain a cut (9.0 g) with the intended kerojet boiling range from 300° F. to 400° F. The actual boiling range for this cut was estimated by simulated distillation analysis ASTM 2887. The boiling range and product properties for this sample were:

| Intended cut 300–400° F. | |
|---|---|
| Boiling Range (°F.) | |
| BP | 166 |
| T10 | 269 |
| T50 | 327 |
| T90 | 379 |
| EP | 454 |
| API gravity | 57.2 |
| Cetane Index | 51 |
| Cetane Number ($^1$H nmr) | 33 |

After cooling, the resulting residua were again distilled under vacuum (about 1–2 torr) to obtain a cut (8.3 g) with the intended diesel fuel boiling range from 400° F. to 650° F. The actual boiling range for this cut was estimated by simulated distillation analysis ASTM 2887. The boiling range and product properties for this sample were:

| Intended cut 400–650° F. | |
|---|---|
| Boiling Range (°F.) | |
| IBP | 302 |
| T10 | 360 |
| T50 | 472 |
| T90 | 577 |
| EP | 646 |
| API gravity | 38.0 |
| Cetane Index | 47 |
| Cetane Number ($^1$H nmr) | 32 |
| wt % Aromatics | 37.5 |

Example 18. This example was performed with the catalyst from the previous example by adjusting the reactor temperature to 374° F. at 600 psig. A pre-mixed isopentane/pentene-1 feed stream (molar ratio=4.8) then was introduced at a flow rate of 0.56 gm pentenes/gmMCM-56/hr. After passing pre-mixed feed through the reactor zone for 50.5 hrs, product was collected over the following 6.5 hrs. Product distributions were calculated from gc analyses of the gaseous and liquid products, and a simulated distillation ASTM 2887 of the residua after rotory evaporation (85° C., ambient atmospheric pressure) of the total liquid products. The total reactor effluent weight was 181.3 g (101.0% mass balance) and showed the following distribution:

| Component | weight % |
| --- | --- |
| C$_3$-minus | 0.01 |
| Isobutane | 0.82 |
| n-Butane | 0.00 |
| Isopentane | 80.76 |
| n-Pentane | 0.51 |
| Cyclopentane | 0.03 |
| C$_6$-paraffin | 0.06 |
| Methylcyclopentane | 0.00 |
| C$_4$-olefin | 0.05 |
| Butadiene | 0.00 |
| C$_5$-olefin | 9.62 |
| Cyclopentene | 0.00 |
| C$_6$-olefin | 0.37 |
| Methylcyclopentane and Benzene | 0.00 |
| C$_7$-plus | 7.77 |
| Total | 100.00 |

Conversion of total C$_5$-olefins was 42.6%. Calculated yields of isobutane and C$_6$-plus components per C$_5$-olefins converted (wt/wt) were:

| Fraction | Yields |
| --- | --- |
| iC4 | 0.12 |
| C$_6$–300° F. | 0.19 |
| 300–400° F. | 0.83 |
| 400–650° F. | 0.12 |
| above 650° F. | 0.00 |
| Total | 1.26 |

About 25 g of squalane was added to a portion (11.6 g) of the rotory evaporation residua to serve as a high boiling "chaser" during fractional microdistillation. After distilling the sample to a 300° F. endpoint at ambient atmospheric pressure, the resulting residua were cooled, then fractionated under vacuum (about 55 torr) to obtain a cut (5.3 g) with the intended kerojet boiling range from 300° F. to 400° F. The actual boiling range for this cut was estimated by simulated distillation analysis ASTM 2887. The boiling range and product properties for this sample were:

| Intended cut 300–400° F. | |
| --- | --- |
| Boiling Range (°F.) | |
| BP | 158 |
| T10 | 298 |
| T50 | 330 |
| T90 | 351 |
| EP | 468 |
| API gravity | 54.9 |

| Intended cut 300–400° F. -continued | |
| --- | --- |
| Cetane Index | 47 |
| Cetane Number ($^1$H nmr) | 13 |

After cooling, the resulting residua were again distilled under vacuum (about 1–2 torr) to obtain a cut (1.1 g) with the intended diesel fuel boiling range from 400° F. to 650° F. The actual boiling range for this cut was estimated by simulated distillation analysis ASTM 2887. The boiling range and product properties for this sample were:

| Intended cut 400–650° F. | |
| --- | --- |
| Boiling Range (°F.) | |
| IBP | 293 |
| T10 | 323 |
| T50 | 455 |
| T90 | 496 |
| EP | 587 |
| API gravity | 46.2 |
| Cetane Index | 59 |
| Cetane Number ($^1$H nmr) | 21 |
| wt % Aromatics | 16.1 |

Changes and modifications in the specifically described embodiments can be carried out without departing from the scope of the invention which is intended to be limited only by the scope of the appended claims.

What is claimed is:

1. A process for converting a feedstock comprising at least one olefin and at least one isoparaffin to product comprising gasoline which comprises contacting said feedstock under conversion conditions with a catalyst composition comprising a porous crystalline material having the structure of MCM-56.

2. A process for converting a feedtstock comprising at least one olefin and at least one isoparaffin to a product comprising distillate which comprises contacting said feedstock under conversion conditions with a catalyst comprising a porous crystalline material having the structure of MCM-56.

3. The process of claim 2, wherein said distillate contains less than about 35 wt. % aromatics.

4. The process of claim 2, wherein said distillate contains less than about 10 wt. % aromatics.

5. The process of claim 2, wherein said distillate has a cetane index of at least about 35.

6. The process of claim 2, wherein said distillate has a cetane index of at least about 45.

7. The process of claim 2, wherein a product fraction boiling at a cut point up to about 450° F. is recycled to the contacting step.

8. The process of claim 2, wherein a product fraction boiling at a cut point up to about 390° F. is recycled to the contacting step.

9. The process of claim 2, wherein said product further comprises gasoline.

10. The process of claim 2, wherein said conversion conditions include a temperature in the range of from about 100°–500° F.; a pressure in the range of from about 0 to about 1500 psig; an olefin WHSV, on zeolite basis, in the range of from about 0.01 to 10; and an isoparaffin:olefin molar ratio in the feedstock in the range of from about 0.1–100.

11. The process of claim 2, wherein said conversion conditions include a temperature in the range of from about 200°–400° F.; a pressure in the range of from about 50 to about 100 psig; an olefin WHSV, on zeolite basis, in the range of from about 0.1 to 5; and an isoparaffin:olefin molar ratio in the feedstock in the range of from about 0.25 to about 50.

12. The process of claim 2, wherein said at least one olefin is selected from the group consisting of $C_3$-$C_{10}$ olefins.

13. The process of claim 12, wherein said at least one olefin is selected from the group consisting of $C_4$-$C_8$ olefins.

14. The process of claim 2, wherein said at least one isoparaffin is selected from the group consisting of $C_4$-$C_8$ isoparaffins.

15. The process of claim 14, wherein said at least one isoparaffin is selected from the group consisting of $C_4$-$C_5$ isoparaffins.

* * * * *